(12) United States Patent
Malberg et al.

(10) Patent No.: US 7,318,839 B2
(45) Date of Patent: Jan. 15, 2008

(54) EXPANDABLE SPINAL IMPLANT

(75) Inventors: Marc I Malberg, Princeton, NJ (US); Gretchen Dougherty Shah, Wayne, NJ (US); Rui J Ferreira, Livingston, NJ (US)

(73) Assignee: EBI, L.P., Parsippany, NJ (US)

( * ) Notice: Subject to any disclaimer, the term of this patent is extended or adjusted under 35 U.S.C. 154(b) by 217 days.

(21) Appl. No.: 10/897,371

(22) Filed: Jul. 22, 2004

(65) Prior Publication Data

US 2005/0021144 A1  Jan. 27, 2005

Related U.S. Application Data

(60) Provisional application No. 60/489,731, filed on Jul. 23, 2003.

(51) Int. Cl.
   *A61F 2/44* (2006.01)

(52) U.S. Cl. .................................. 623/17.11

(58) Field of Classification Search ... 623/17.11–17.16
   See application file for complete search history.

(56) References Cited

U.S. PATENT DOCUMENTS

| | | |
|---|---|---|
| 5,192,327 A | 3/1993 | Brantigan |
| 5,397,364 A | 3/1995 | Kozak et al. |
| 5,554,191 A | 9/1996 | Lahille et al. |
| 5,658,337 A | 8/1997 | Kohrs et al. |
| 5,865,848 A | 2/1999 | Baker |
| 6,039,761 A | 3/2000 | Li et al. |
| 6,126,689 A | 10/2000 | Brett |
| 6,159,211 A | 12/2000 | Boriani et al. |
| 6,159,245 A | 12/2000 | Meriwether et al. |
| 6,179,873 B1 | 1/2001 | Zientek |
| 6,179,875 B1 | 1/2001 | Von Strempel |
| 6,190,414 B1 | 2/2001 | Young et al. |
| 6,193,757 B1 | 2/2001 | Foley et al. |
| 6,210,442 B1 | 4/2001 | Wing et al. |
| 6,241,769 B1 | 6/2001 | Nicholson et al. |
| 6,251,140 B1 | 6/2001 | Marino et al. |
| 6,454,807 B1 | 9/2002 | Jackson |
| 2004/0254643 A1* | 12/2004 | Jackson ................ 623/17.11 |

FOREIGN PATENT DOCUMENTS

| | | |
|---|---|---|
| FR | 2 717 068 | 9/1995 |
| WO | WO 00/25706 | 5/2000 |
| WO | WO 01/01895 A1 | 1/2001 |
| WO | WO 02/05733 A1 | 1/2002 |

\* cited by examiner

*Primary Examiner*—Bruce Snow
(74) *Attorney, Agent, or Firm*—Harness, Dickey & Pierce, P.L.C.

(57) ABSTRACT

An expandable spinal implant including a first member and a second member. The first member has first and second arms. The first and second arms of the first member both including an upper face partially defining an upper contact area of the implant and a lower face partially defining a lower contact surface of the implant. The second member has first and second arms that both include an upper face partially defining an upper contact area of the implant and a lower face partially defining a lower contact surface of the implant. The first and second members are pivotally coupled to each other for relative movement about a rotation axis between a closed position for inserting the implant into a spine and an expanded position for providing structural support to the spine. The rotation axis extends generally perpendicular to the upper and lower contact surfaces.

21 Claims, 6 Drawing Sheets

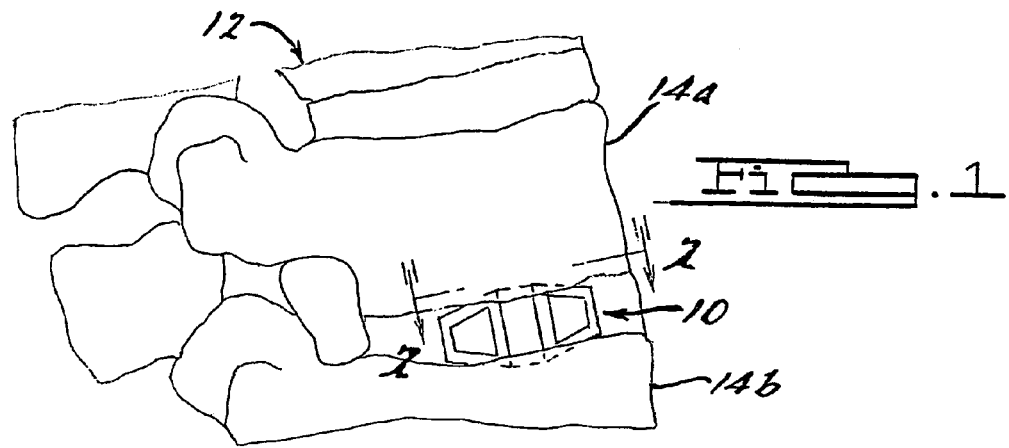
FIG. 1
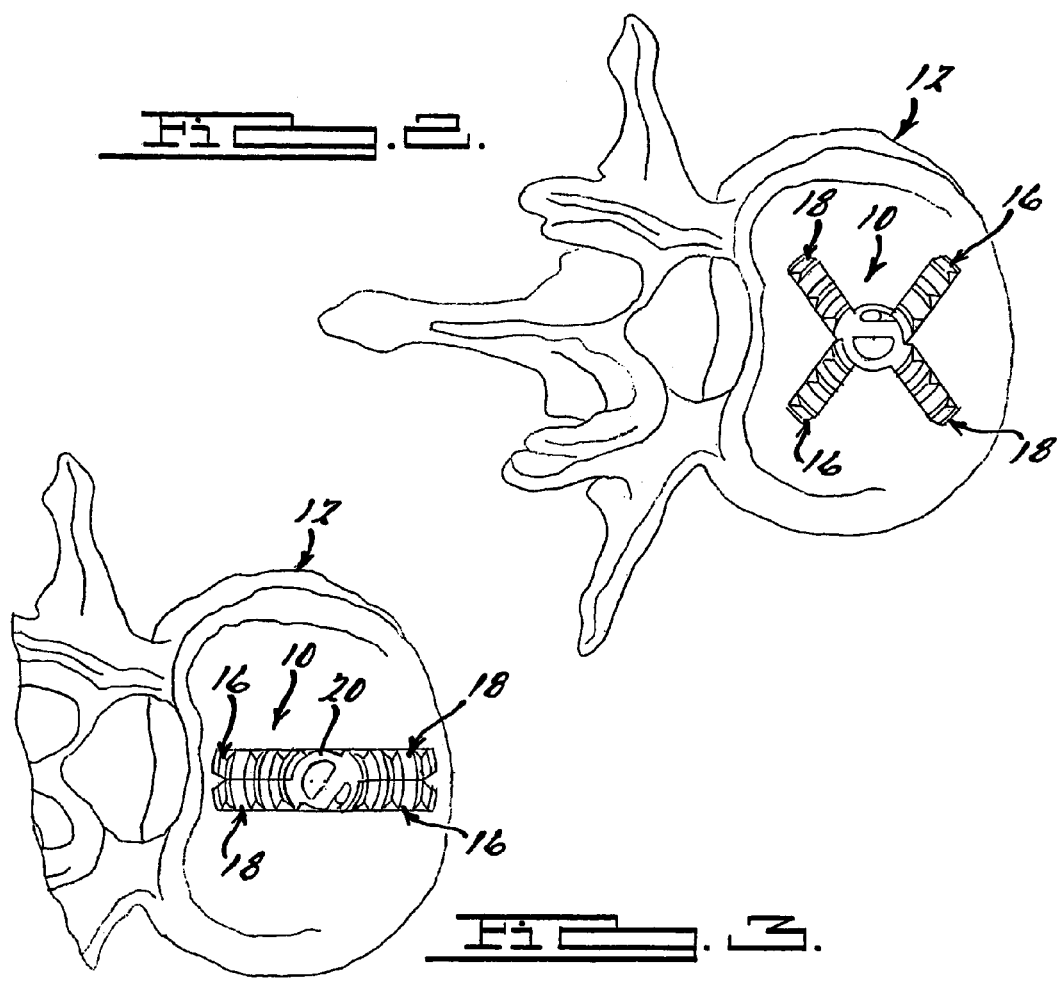
FIG. 2
FIG. 3

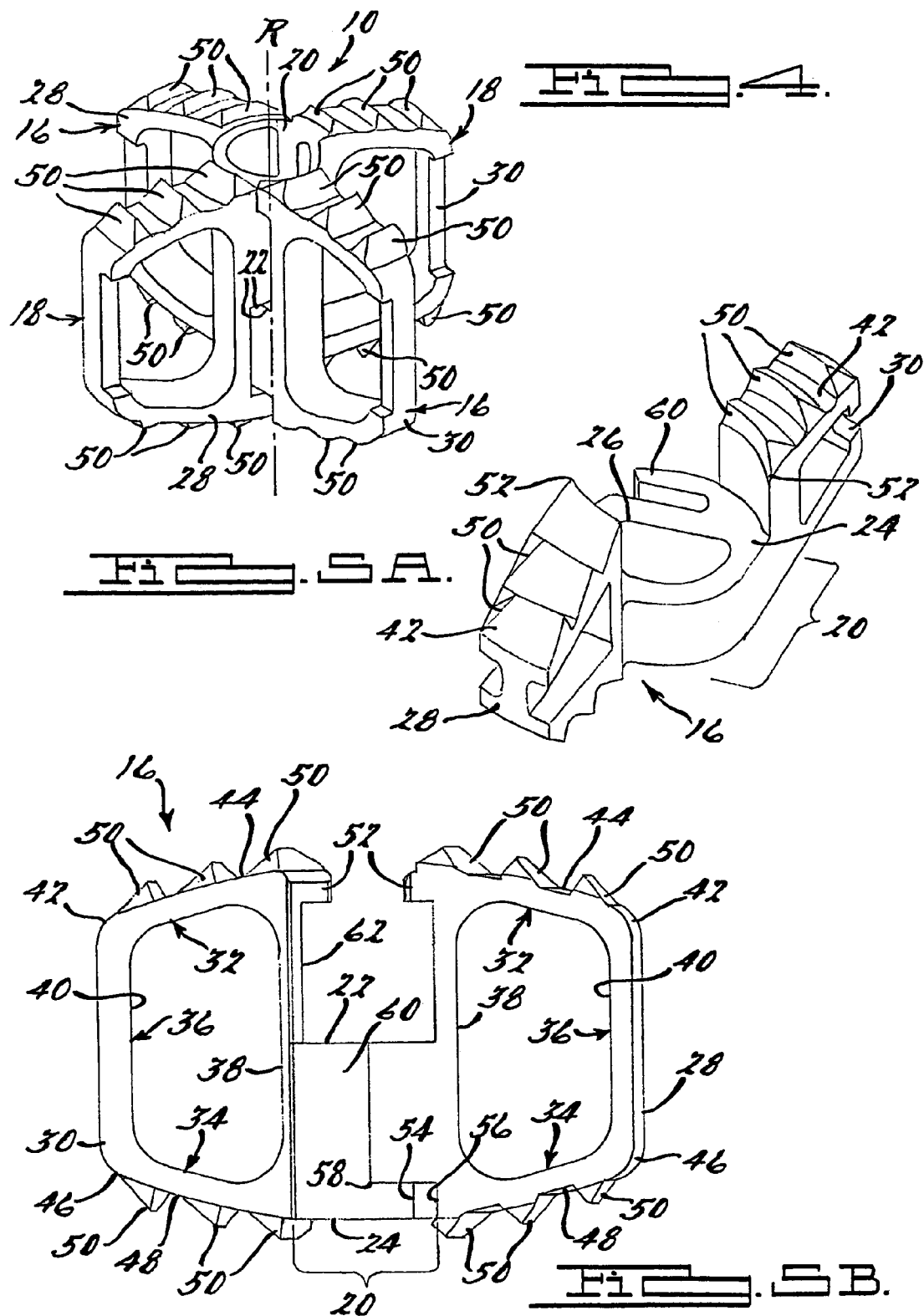

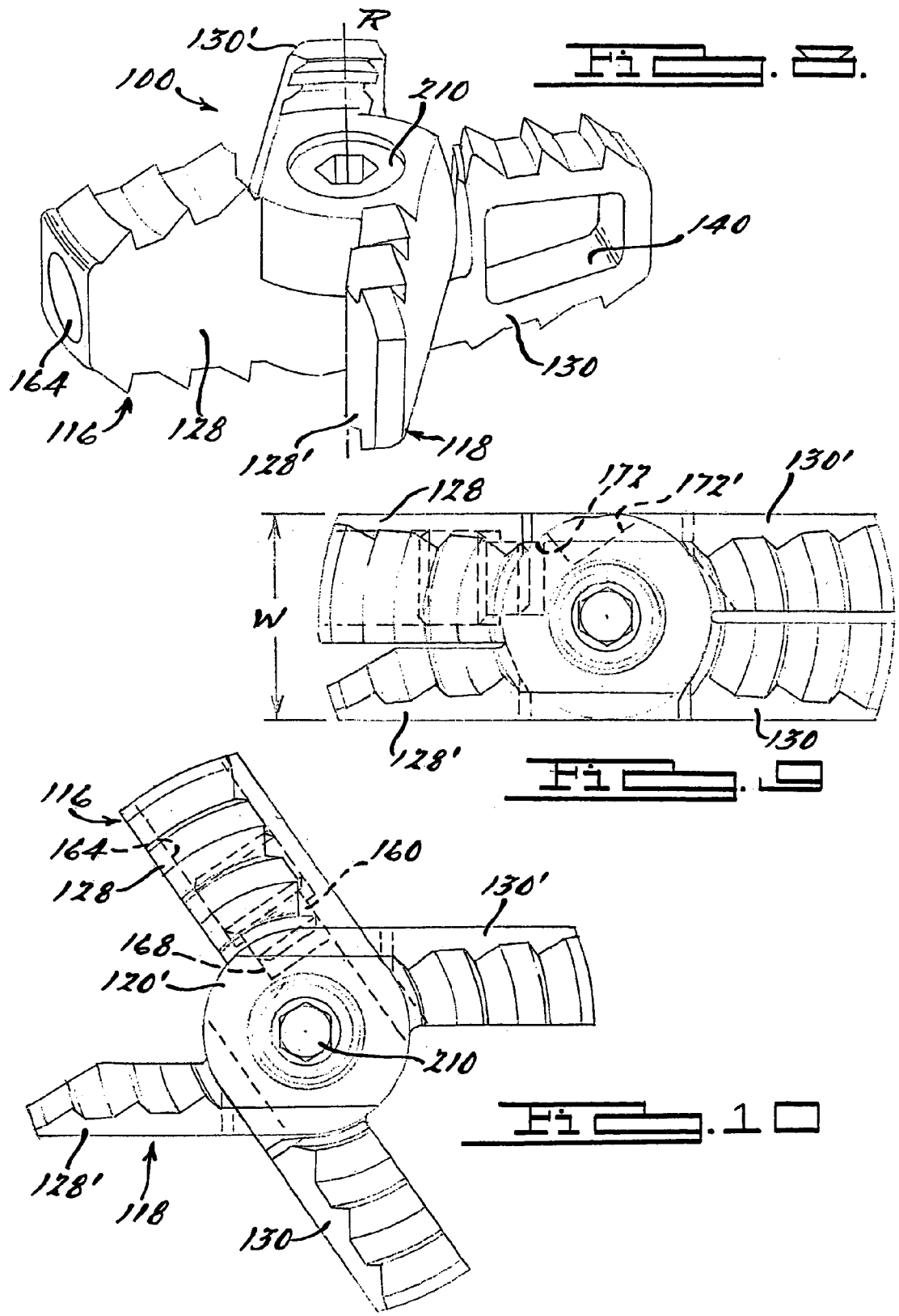

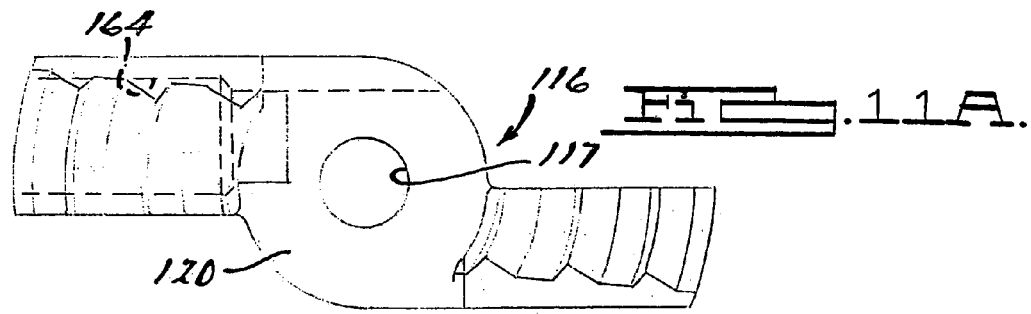
FIG. 11A.
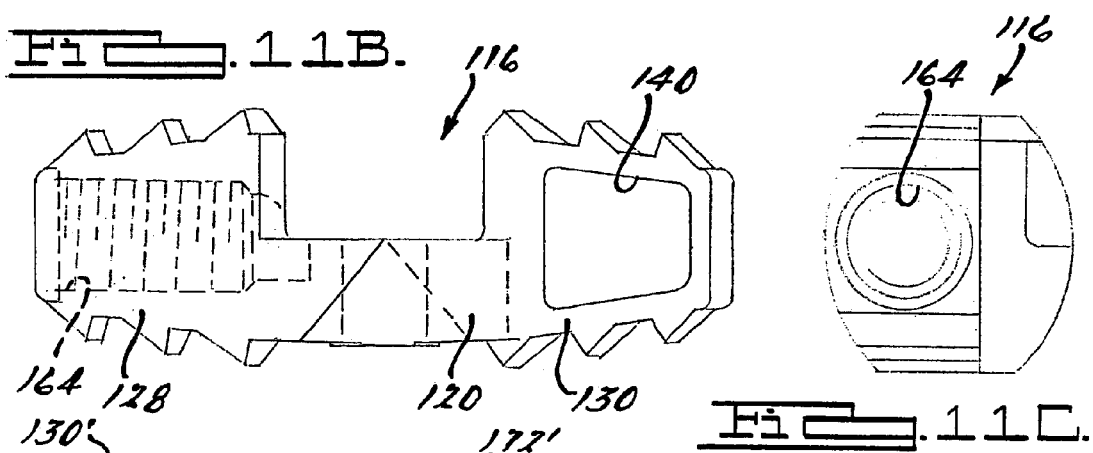
FIG. 11B.
FIG. 11C.
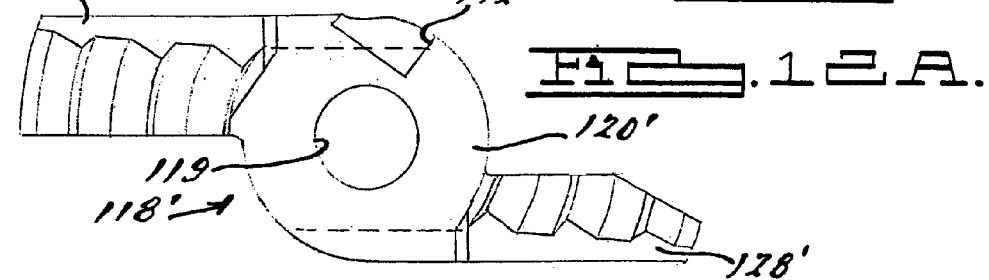
FIG. 12A.
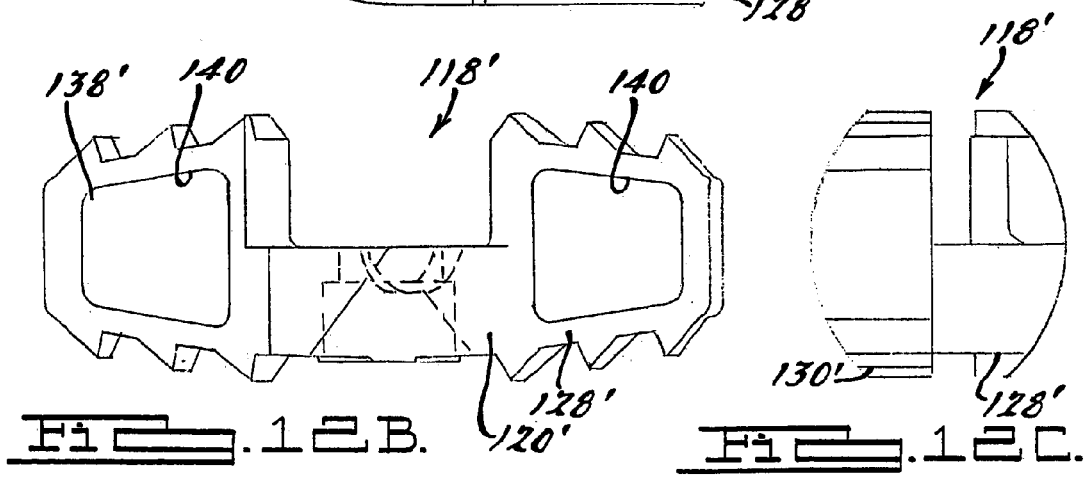
FIG. 12B.
FIG. 12C.

EXPANDABLE SPINAL IMPLANT

CROSS-REFERENCE TO RELATED APPLICATIONS

This application claims the benefit of U.S. Provisional Application No. 60/489,731, filed on Jul. 23, 2003. The disclosure of the above application is incorporated herein by reference.

BACKGROUND OF THE INVENTION

The spinal column is a highly complex structure which houses and protects critical elements of the nervous system. In spite of these complexities, the spinal column is a highly flexible structure, capable of a high degree of curvature and twist through a wide range motion. Genetic or developmental irregularities, trauma, chronic stress, tumors, and disease, however, can result in spinal pathologies which either limit this range of motion, or threaten the critical elements of the nervous system housed within the spinal column.

In various orthopedic surgical procedures, it is necessary to stabilize portions of a spinal column relative to one another. This need is typically a result of disease, damage or congenital deformation. In one method of treatment for intervertebral disk degeneration, the normal gap between adjacent vertebral bodies is surgically re-established and maintained with a rigid spacer inserted between the bodies. The rigid spacer is filled with bone graft material to facilitate bony fusion of the two vertebral bodies. A successful fusion stabilizes the spine, reduces pressure on the spinal cord and nerve roots, and reduces or eliminates back pain.

While known devices for spinal fusion have proven to be effective in various applications, there remains a need for spinal implants that do not require large incisions for implantation, that can relieve localized stress on adjacent vertebral end plates, and that can prevent migration and retropulsion within the spinal column.

SUMMARY

The present teachings provide an expandable spinal implant including a first member and a second member. The first member has first and second arms. The first and second arms of the first member both including an upper face partially defining an upper contact area of the implant and a lower face partially defining a lower contact surface of the implant. The second member has first and second arms that both include an upper face partially defining an upper contact area of the implant and a lower face partially defining a lower contact surface of the implant. The first and second members are pivotally coupled to each other for relative movement about a rotation axis between a closed position for inserting the implant into a spine and an expanded position for providing structural support to the spine. The rotation axis extends generally perpendicular to the upper and lower contact surfaces.

The present teachings also provide an expandable spinal implant having first and second members both with a central portion and first and second arms extending from the central portion. The central portion of the second member is coupled to the central portion of the first member for rotation about a rotation axis between a closed orientation for insertion into a spine and an expanded orientation for providing structural support to the spine. The spinal implant further includes a locking mechanism for arresting relative movement between the first member and the second member.

The present teachings provide a method of stabilizing a portion of a spine. The method includes providing a spinal implant having a first elongated member and a second elongated member. The first elongated member has a central portion rotatably coupled to a central portion of the second elongated member for rotation between a closed position and an expanded position. The method additionally includes orienting the first and second elongated members in the closed position and inserting the spinal implant into the spine between first and second vertebral bodies. The rotation axis is vertically oriented. The method further includes rotating the first and second elongated members to the expanded position while the spinal implant is within the spine.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a side view of an expandable spinal implant constructed in accordance with the present teachings, the expandable spinal implant shown operatively positioned between vertebral bodies of a human spine;

FIG. 2 is a cross-sectional view taken along the line 2—2 of FIG. 1, the expandable spinal implant shown in an expanded or open condition;

FIG. 3 is a cross-sectional view similar to FIG. 2, the expandable spinal implant shown in a contracted or closed condition to facilitate insertion into the spine;

FIG. 4 is a perspective view of an expandable spinal implant according to the present teachings, and shown removed from the spine for purposes of illustration;

FIG. 5A is a top perspective view of a first member of the expandable spinal implant of FIG. 4;

FIG. 5B is a side view the first member of the expandable spinal implant of FIG. 4;

FIG. 8 is a perspective view of an expandable spine implant according to the present teachings, shown in the open position;

FIG. 9 is a top view of the expandable spine implant of FIG. 8, shown in the closed position;

FIG. 10 is a top view of the expandable spine implant of FIG. 8, shown in the open position;

FIG. 11A is a top view of a first member of the expandable spine implant of FIG. 8;

FIG. 11B is a side view of the first member of the expandable spine implant of FIG. 8;

FIG. 11C is an end view of the first member of the expandable spine implant of FIG. 8;

FIG. 12A is a top view of a second member of the expandable spine implant of FIG. 8;

FIG. 12B is a side view of the second member of the expandable spine implant of FIG. 8;

FIG. 12C is an end view of the second member of the expandable spine implant of FIG. 8;

DETAILED DESCRIPTION

Figure 5C:
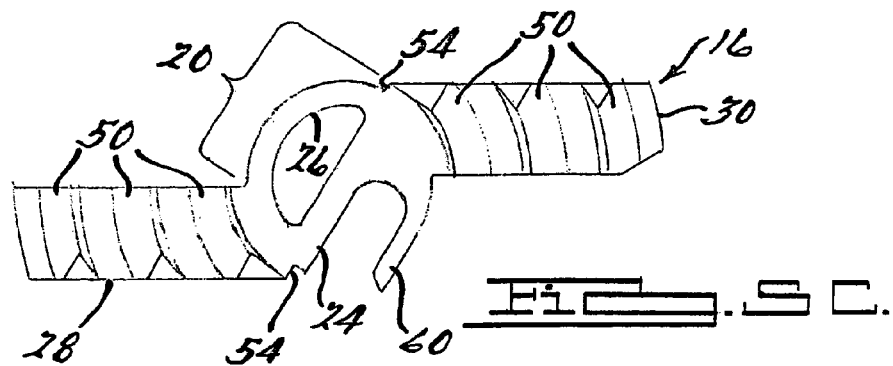
FIG. 5C is a bottom view of the first member of the expandable spinal implant of FIG. 4.

The following description of various embodiments is merely exemplary in nature and is in no way intended to limit the invention, its application, or uses.

With initial reference to FIG. 1 and FIG. 2, an exemplary spinal implant constructed in accordance with the present teachings is illustrated and generally identified at reference number 10. The spinal implant 10 is shown operatively associated with a human spinal column 12. More specifically, the spinal implant 10 is shown positioned between a first vertebra 14a and a second vertebra 14b to stabilize the spine 12.

With continued reference to the environmental views of FIGS. 1 and 2 and additional reference to FIGS. 3 through 7, the spinal implant 10 of the present invention will be addressed in detail. The spinal implant 10 is illustrated to generally include a first member or first elongated member 16 and a second member or second elongated member 18. As will become more apparent below, the first elongated member 16 and the second elongated member 18 are completely separate members and are coupled to one another for relative movement between a closed position or orientation (shown in FIG. 3) and an expanded position or orientation (shown in FIG. 2). As will be appreciated more fully below, the closed orientation facilitates insertion of the spinal implant 10 within the spine 12 through a small incision, while the expanded orientation disperses the load on the adjacent end plates.

With particular reference to FIG. 4, the implant 10 is shown removed from the spine 12 for purposes of illustration and articulated to the open position. As shown in FIG. 4, the first elongated member 16 and the second elongated member 18 can be substantially identical to each other. For this reason, a description of the first elongated member 16 will serve to fully describe both the first elongated member 16 and the second elongated member 18 for the exemplary implant 10. In view of this similarity, like reference numbers for implant 10 will be used throughout FIGS. 1–7 to identify common elements of the first elongated member 16 and the second elongated member 18. It will be appreciated, however, that the first and second elongated members need not be identical, as is illustrated in FIGS. 8–14 for another exemplary implant 100 described below.

Various different views of the first elongated member 16 are provided in FIGS. 5A through 5C in which the first elongated member 16 is separated from the second elongated member 18. As seen in FIGS. 5A–5C, the first elongated member 16 is illustrated to include a central or intermediate portion 20. The central portion 20 is generally circular and upwardly extends from a lower surface of the implant. The central portion 20 has a height equal to approximately one-half the height of the implant 10. As a result, an upper or inner surface 22 of the central portion 20 is disposed at approximately a horizontal mid-line of the implant 10. The central portion 20 also includes a lower or outer surface 24.

Extending through the central portion 20, between the upper surface 22 and the lower surface 24, is a through slot 26. The through slot 26 permits bone ingrowth through the implant 10 to more rigidly secure the implant 10 within the spine 12. The through slot 26 also reduces the weight of the implant 10 while maintaining the strength of the implant 10. Further, the through slot 26 allows the implant 10 to be easily held and positioned by a physician using suitable medical instrumentation.

Extending from opposite sides of the central portion 20 are a first arm 28 and a second arm 30. In the embodiment illustrated, the first arm 28 and the second arm 30 are identical and generally extend tangentially from the central portion 20. The first arm 28 and the second arm 30 preferably extend from the central portion 20 parallel to each other, but are slightly offset from each other. As seen best FIG. 5B, the first arm 28 and the second arm 30 each include an upper wall 32, a lower wall 34, an outer wall 36, and an inner wall 38. The inner wall 38 extends from the lower surface 24 of the central portion 20 to a distance that is twice the distance between the upper surface 22 and the lower surface 24 to accommodate the central portion 20 of the second elongated member 18, as described below. In this regard, a cavity is effectively defined to receive the central portion 20 of the second elongated portion 18.

As seen most clearly in FIG. 5B, within both the first arm 28 and the second arm 30 is a center opening or window 40. The window 40 is defined by the upper wall 32, the lower wall 34, the outer wall 36, and the inner wall 38. The window 40 reduces the weight of the implant 10 and permits bone ingrowth through the first arm 28 and the second arm 30 to better secure the implant 10 within the spine 12.

The upper wall 32 includes an upper face 42 that partially defines an upper contact surface 44. The lower wall 34 includes a lower face 46 that partially defines a lower contact surface 48. The upper contact surface 44 and the lower contact surface 48 are preferably convex in shape. Alternatively, the upper and lower contact surfaces 44 and 48 may be flat or conically shaped.

Figure 7:
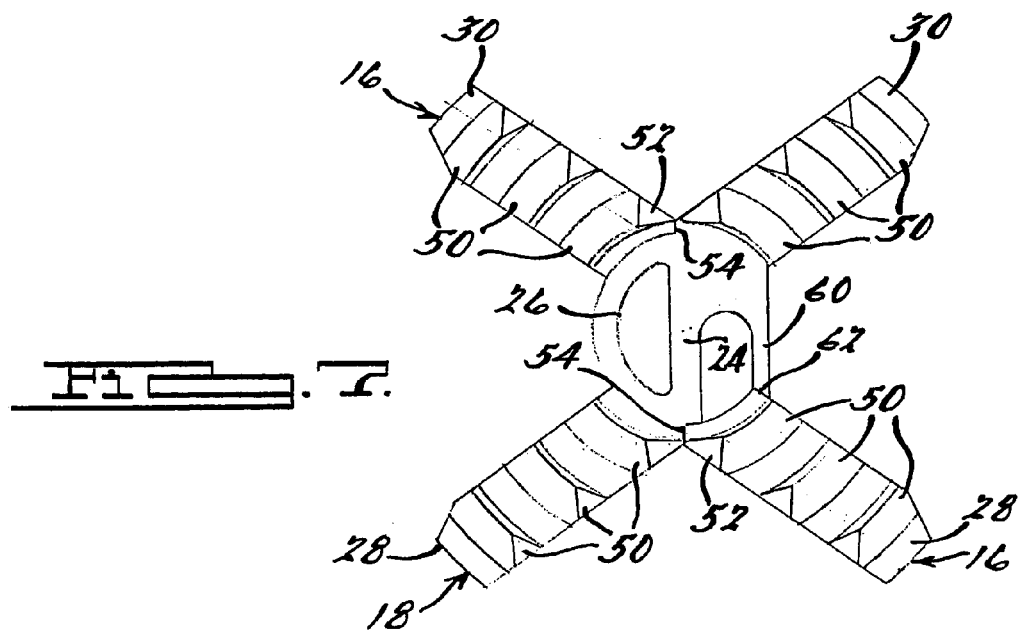
FIG. 7 is a top view of the expandable spinal implant of FIG. 4, shown in the open position.

Both the upper contact surface 44 and the lower contact surface 48 are preferably formed to include a plurality of teeth 50. The teeth 50 extend towards the central portion 20. When the implant 10 is in its expanded orientation (as shown in FIG. 7, for example), the teeth 50 of the various arms 28 and 30 of the implant 10 are concentrically arranged. Further, as seen most clearly in FIG. 5A, the teeth 50 are ramped in the direction of expansion of the implant 10 from the closed position to the open position to ease the expansion of the implant 10 and to ease the insertion of the implant 10 within the spine 12. The ramped teeth 50 function to prevent the implant 10 from migrating and prevent retropulsion from the spine.

Figure 6:
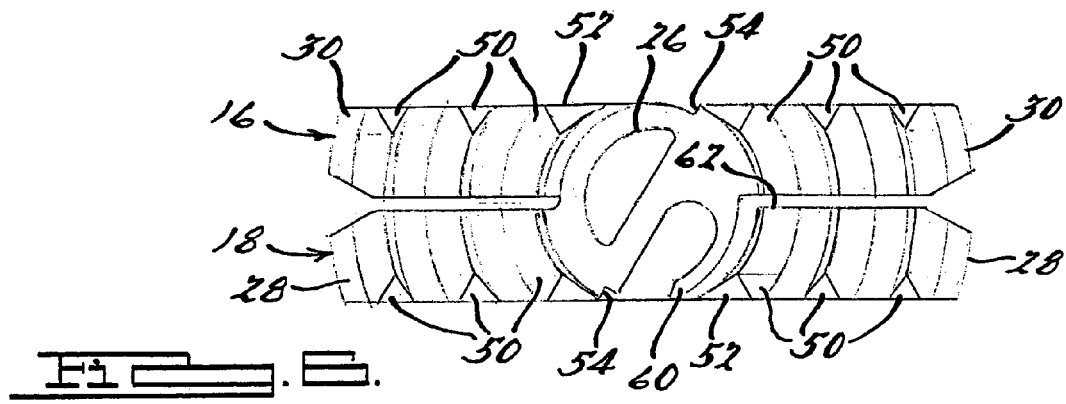
FIG. 6 is a top view of the expandable spinal implant of FIG. 4, shown in the closed position.

With particular reference to FIG. 4, FIG. 6, and FIG. 7, the coupling of the first elongated member 16 with the second elongated member 18 will now be described. The first elongated member 16 and the second elongated member 18 are coupled such that the inner surface 22 of the first member 16 and the inner surface 22 of the second member 18 are in contact with each other. Further, the first arm 28 and the second arm 30 of the first elongated member 16 are each positioned between the first arm 28 and the second arm 30 of the second elongated member 18 such that the arms 28 and 30 of the first elongated member 16 alternate with the arms 28 and 30 of the second elongated member 18.

The first member 16 and the second member 18 are pivotally coupled to each other for relative movement about a rotation axis R (identified in FIG. 4). The rotation axis R extends through the central portion 20, generally perpendicular to the upper contact surface 44 and the lower contact surface 48. This pivotal coupling permits relative rotation of the first member 16 and the second member 18 between the closed position and the open position. The first member 16 and the second member 18 are typically rotated between the closed position and the open position by a surgeon using appropriate operating room instrumentation.

The elongated members 16 and 18 are illustrated coupled together in the closed position in FIG. 6. In the closed position, the first arm 28 of the first elongated member 16 is positioned parallel to and adjacent to the second arm 30 of the second elongated member 18. Further, the second arm 30 of the first member 16 is positioned parallel to and adjacent to the first arm 28 of the second elongated member 18. Positioning the arms 28 and 30 of the first elongated member 16 parallel to and adjacent to the arms 28 and 30 of the second elongated member 18 provides the implant 10 with a slim and compact profile that permits the implant 10 to be easily inserted within the spine 12 requiring only a minimal disruption of the vertebrae 14 and the dura (not shown).

With particular reference to FIG. 4 and FIG. 7, the first elongated member 16 and the second elongated member 18 are shown coupled together in the open position. In the open position the first arm 28 of the first elongated member 16 is positioned apart from and in a non-parallel relationship to the second arm 30 of the second elongated member 18. Likewise, the second arm 30 of the first member 16 is positioned apart from and in a non-parallel relationship to the first arm 28 of the second elongated member 18. Generally, in the open position the first member 16 and the second member 18 are rotated such that the arms 28 and 30 of the first member 16 and the arms 28 and 30 of the second member 18 have an overall configuration approximating that of an "X". This "X" shaped configuration provides the implant 10 with a great deal of strength to support the vertebrae 14 of the spine 12.

The first elongated member 16 and the second elongated member 18 each further comprise a pair of protrusions 52 and a pair cooperating of recesses 54. The protrusions 52 extend from the upper face 42 and the recesses 54 are located within the outer surface 24 of the central portion 20. The recesses 54 have a sidewall 56 and a retention surface 58 (see FIG. 5B). As the first and second elongated members 16 and 18 are rotated from the closed position to the open position, the protrusions 52 rotate within the recesses 54 such that each protrusion 52 contacts both the sidewall 56 and the retention surface 58.

As seen most clearly in FIG. 4A and FIG. 7, cooperation between the protrusions 52 of the first elongated member 16 and the recesses 54 of the second elongated member 18, as well as cooperation between the protrusions 52 of the second elongated member 18 and the recesses 54 of the first elongated member 16, ensures that the first elongated member 16 stays coupled to the second elongated member 18 when the implant 10 is in the open position. Specifically, interaction between the protrusions 52 and the retention surface 58 prevents the first member 16 and the second member 18 from becoming vertically separated along the rotational axis R of the implant 10.

To secure the implant 10 in the open position, the implant 10 further includes a locking mechanism. The locking mechanism is preferably an active locking mechanism comprised of an arm or detail 60 that extends from the central portion 20 of both the first member 16 and the second member 18. The detail 60 is flexible, preferably a leaf spring, and can be moved between a neutral position (as shown in FIG. 5C) and a collapsed position (as shown in FIG. 6).

As seen in FIG. 6, in the closed position the detail 60 of the second member 18 is resiliently collapsed against the inner wall 38 of the first member 16. Likewise, in the closed position the detail 60 of the first member 16 is resiliently collapsed against the inner wall 38 of the second member 18 (not particularly shown). As the first member 16 and the second member 18 are rotated from the closed position to the open position, the details 60 and 60 resiliently return from beyond the inner walls 38 and 38 respectively.

In the open position the details 60 automatically extend into their neutral positions as the details 60 are no longer restricted by the inner walls 38. In its neutral position, the detail 60 of the first elongated member 16 abuts an outer surface 62 of the inner wall 38 of the second elongated member 16. Similarly, the detail 60 of the second elongated member 18 abuts an outer surface 62 of the inner wall 38 of the first elongated member 14 to prevent the implant 10 from returning to its closed position. The implant 10 can only be returned to the closed position if pressure is applied to the details 60 to return them to their collapsed state where they no longer contact the corresponding outer surfaces 62 respectively and can each again recede beneath the inner wall 38 of the opposite elongated of member 14 or 16.

An exemplary implantation of the implant 10 of the present invention within the spine 12 will now be described. Before the implant 10 is inserted, the spine 12 must be prepared to receive the implant 10 by the operating surgeon. Preparation of the spine 12 involves making a small incision posteriorly within the dura. The adjacent vertebrae 14 are distracted to return normal spacing and the intevetrabal disk is removed. Once the spine 12 has been prepared, the implant 10, orientated in the closed position, is inserted between the first vertebra 14a and the second vertebra 14b. To insert the implant 10 in the closed position requires only a small incision in the dura matter and only minimal distraction of the spine 12, thus maintaining the integrity of the vertebrae 14 and permitting the surgeon to make the most efficient use of operating room time. When positioned in the open orientation (FIG. 2), the spinal implant 10 stabilizes the spine 12 and facilitates the fusion of a pair of adjacent vertebrae 14.

After the implant 10 is properly installed within the spine 12, the first member 16 and the second member 18 are rotated from the closed position to the open position so that the implant 10 may provide the required support between the adjacent vertebrae 14. Rotation of the implant 10 from the closed position is effectuated by the attending surgeon using suitable operating room instrumentation. The implant 10 is maintained in the open position through interaction between the details 60 and the cooperating outer surfaces respectively.

Rotation of the implant 10 into the open position is facilitated by the ramped teeth 50, which are ramped in the direction of the expansion of the implant 10 from the closed position to the open position. The ramped teeth 50 also help maintain the implant 10 in the open position. Further, the ramped teeth 50 help maintain the implant 10 in its proper position between the vertebrae 14.

Adjacent vertebrae 14 may optionally be supported by multiple implants 10. The process for inserting multiple implants 10 is substantially identical to the process described above for inserting a single implant 10, with the exception being that at least one additional implant 10 is inserted between the vertebrae 14 during the insertion process. The use of multiple implants 10 is advantageous as multiple implants 10 provide additional support to the vertebrae 14 to further disperse stress loads.

The implant 10 may be of various different sizes to properly fit patients having spines 12 and vertebrae 14 of different sizes. The size of the implant 10 may vary in numerous different ways. For example, the first elongated member 16 and the second elongated member 18 may be of various different lengths to support vertebrae 14 of different surface areas. Further, the first elongated member 16, the second elongated member 18, and the central portions 20 may be of different heights to support vertebrae 14 that are spaced at varying distances from each other.

The implant 10, may be manufactured from any biocompatible material that is suitably rigid to withstand the pressures exerted upon the implant 10 by the vertebrae 14. Examples of materials that may be used to manufacture the implant 10 include, but are not limited to, titanium and allograft bone. As shown throughout the drawings, the first member 16, and the second member 18, each preferably comprise a single unitary structure.

Referring to FIGS. 8–14, another exemplary spinal implant 100 according to the present teachings is illustrated. Elements of implant 100 that correspond in some fashion to elements of implant 10 are designated with the same reference numbers, but prefaced by the numeral 1. Detailed repetitious description of elements or features that can be identical in implants 10 and 100 is omitted.

Referring to FIGS. 8–10, the implant 100 includes first and second elongated members 116, 118 pivotably connected to each other by a pivot member 210 for relative rotation therebetween about a pivot axis R, such that the implant 100 can be expanded from a closed orientation illustrated in FIG. 9 to an open (expanded) orientation illustrated in FIG. 10. In the closed orientation, the first and second members 116, 118 are substantially parallel, while in the open orientation the first and second members 116, 118 are at an angle defining substantially an "X" shape. The first elongated member 116 has first and second arms 128, 130 that interconnect with a central portion 120. The second elongated member has first and second arms 128', 130' that interconnect with a central portion 120'. Recesses 172, 172' are defined respectively in the central portions 120, 120' of the first and second members 116, 118, such that the recesses 172, 172' are offset in the closed orientation, and aligned in open orientation.

Figure 13A:
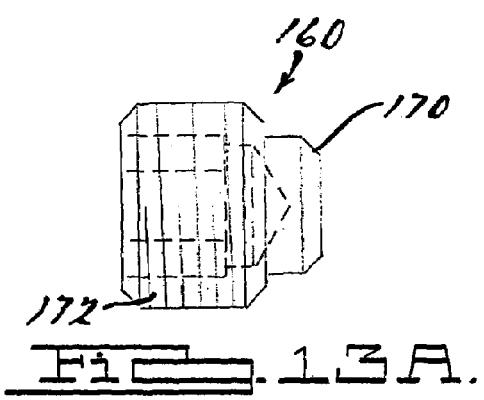
FIG. 13A is a side view of a locking member of the expandable spine implant of FIG. 8.
Figure 13B:
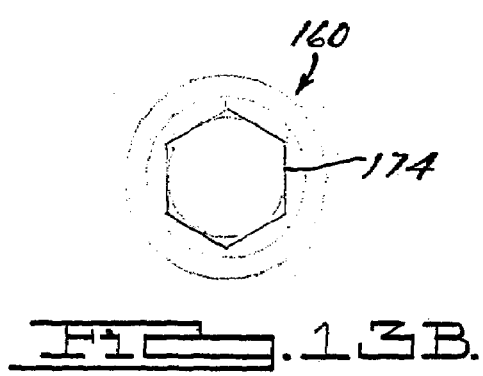
FIG. 13B is an end view of the locking member of the expandable spine implant of FIG. 8.

Referring to FIGS. 11A–C and 14A–B, the first arm 128 of the first elongated member 116, or, more generally, at least one of the arms, 128, 130, 128', 130', can be adapted to define an internally threaded bore 164 for accommodating a locking member 160 therein. The locking member 160 can be a fastener, such as an externally threaded screw, as illustrated in FIGS. 13A and 13B, and can be threadably engaged with the internal threads of the bore 164.

The locking member 160 can include an end portion or boss 170 and a head 172 with an engagement formation or surface 174. The locking member 160 can be deployed to secure the implant 100 in the open orientation by engaging the first arm 128 of the first member 116 with the central portion 120' of the second member 118, when the implant 100 is in the open orientation. In the open orientation, the recesses 172, 172' in the central portions 120, 120' of the first and second members 116, 118 become aligned and define a hole 168 that receives an end portion 170 of the locking member 160. The locking member 160 can be deployed using a driver or similar tool that is inserted into the internal bore 164 of the first arm 128 and operated to engage the engagement formation 174 and to rotate the locking member 160, thereby causing the locking member 160 to advance into the hole 128 and positively secure the implant 100 in the open orientation.

Figure 14A:
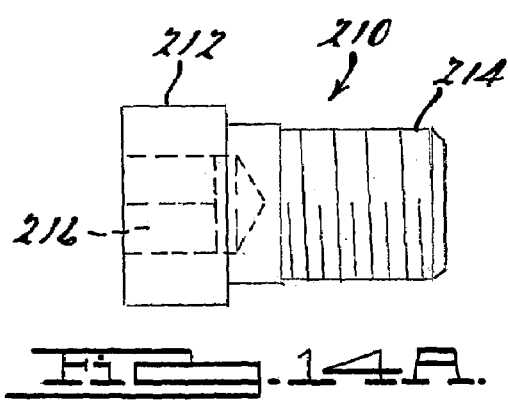
FIG. 14A is a side view of a pivot member of the expandable spine implant of FIG. 8.
Figure 14B:
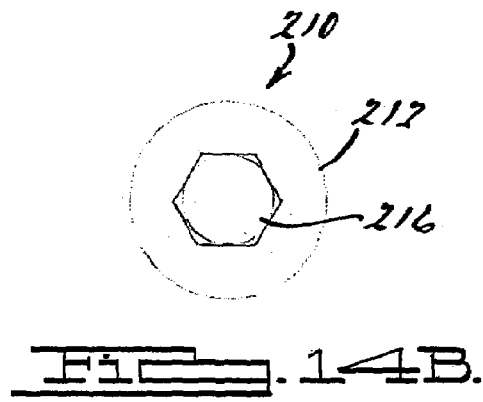
FIG. 14B is an end view of the pivot member of the expandable spine implant of FIG. 8.

Referring to FIGS. 14A and B, the pivot member 210 can be, for example, a fastener, such as screw or bolt, that engages openings 117, 119 in the respective the central portions 120, 120' of the first and second members 116, 118 for relative rotation therebetween. The pivot member 210 can include a head 212 and a stepped shank 214 that is received into the central openings 117, 119 of the central portions 120, 120' of the first and second members 116, 118. The pivot member 210 can include a head formation 216 for receiving a tool for rotating the first and second members from the closed orientation to the open orientation after implantation.

Referring to FIGS. 11B and 12B, all except the first arm 128 of the first member 116 can include openings or windows 140 to promote ingrowth. The second arms 130, 130' of the first and second members 1116, 118 can be identical. The first arm 128' of the first member 116 can be wider in cross-section than the first arm 128' of the second member 118 for accommodating the internal bore 164 that receives the locking member 160, although the implant 100 in the closed orientation can have substantially constant total W, as shown in FIG. 9. The threaded bore 164 of the first arm 128 can receive an instrument for inserting/deploying the implant 100. The top and bottom surfaces of the arms 128, 130, 128', 130' can include a plurality of teeth 150 for engaging adjacent vertebrae as described above in connection with exemplary implant 10.

Similarly to implant 10, implant 100 can be inserted in the spine 12 in the closed orientation through a small incision. After implantation, the first and second members 116, 117 are pivoted about the central axis R relative to each other to bring the implant 100 to the open orientation. The implant 100 is then positively locked in the open orientation by deploying the locking member 160 using a suitable driver or tool.

It will be appreciated that implants 10 and 100 are merely exemplary illustrations, such that various features of exemplary implant 10 can be incorporated in exemplary implant 100, and vice versa.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An expandable spinal implant comprising:
   a first member having first and second arms, the first and second arms of the first member both including an upper face partially defining an upper contact area of the implant and a lower face partially defining a lower contact surface of the implant; and
   a second member having first and second arms, the first and second arms of the second member both including an upper face partially defining an upper contact area of the implant and a lower face partially defining a lower contact surface of the implant, the second member being completely separate from the first member;
   the first and second members coupled to each other such that the first and second arms of the first member alternate with the first and second arms of the second member, the first and second members pivotally coupled to each other for relative movement about a rotation axis between a closed position for inserting the implant into a spine and an expanded position for providing structural support to the spine, the rotation axis extending generally perpendicular to the upper and lower contact surfaces, wherein the first and second members both include a central portion between the respective first and second arms, the central portions of the first and second members being rotatably coupled.

2. The expandable spinal implant of claim 1, wherein the first and second arms of the first member are parallel and transversely spaced apart relative to one another and the first and second arms of the second member are parallel and spaced apart relative to one another.

3. The expandable spinal implant of claim 1, wherein the first arm of the first member is parallel to and adjacent the second arm of the second member in the closed position.

4. The expandable spinal implant of claim 1, wherein each of the arms defines a window to facilitate bone ingrowth.

5. The expandable spinal implant of claim 1, wherein the first and second members are constructed of allograft bone.

6. The expandable implant of claim 1, further comprising a locking mechanism for arresting relative movement between the first and second members.

7. The expandable spinal implant of claim 6, wherein the locking mechanism automatically arrests relative movement between the first and second members in response to movement from the closed position to the expanded position.

8. The expandable spinal implant of claim 7, wherein the first and second members are substantially identical.

9. An expandable spinal implant comprising:
a first member having first and second arms, the first and second arms of the first member both including an upper face partially defining an upper contact area of the implant and a lower face partially defining a lower contact surface of the implant; and
a second member having first and second arms, the first and second arms of the second member both including an upper face partially defining an upper contact area of the implant and a lower face partially defining a lower contact surface of the implant, the second member being completely separate from the first member;
the first and second members coupled to each other such that the first and second arms of the first member alternate with the first and second arms of the second member, the first and second members pivotally coupled to each other for relative movement about a rotation axis between a closed position for inserting the implant into a spine and an expanded position for providing structural support to the spine, the rotation axis extending generally perpendicular to the upper and lower contact surfaces, wherein each of the upper faces of the first and second arms of the first member and the first and second arms of the second member defines a plurality of teeth, the teeth being concentrically oriented when the first and second members are rotated to the expanded position.

10. An expandable spinal implant comprising:
a first member having a central portion and first and second arms extending from the central portion of the first member;
a second member having a central portion and first and second arms extending from the central portion of the second member, the central portion of the second member coupled to the central portion of the first member for rotation about a rotation axis between a closed orientation for insertion into a spine and an expanded orientation for providing structural support to the spine; and
a locking mechanism comprising a leaf spring for arresting relative movement between the first member and the second member.

11. The expandable spinal implant of claim 10, wherein the locking mechanism is an active locking mechanism for automatically arresting relative movement between the first and second members in response to rotation from the closed orientation to the expanded orientation.

12. The expandable spinal implant of claim 10, wherein the locking mechanism is integrally formed with at least one of the first and second members.

13. An expandable spinal implant comprising:
a first member having a central portion and first and second arms extending from the central portion of the first member;
a second member having a central portion and first and second arms extending from the central portion of the second member, the central portion of the second member coupled to the central portion of the first member for rotation about a rotation axis between a closed orientation for insertion into a spine and an expanded orientation for providing structural support to the spine; and
a locking mechanism for arresting relative movement between the first member and the second member, wherein the locking mechanism is integrally formed with at least one of the first and second members, and wherein the locking mechanism comprises a leaf spring that migrates to a neutral state in response to relative rotation of the first and second members from the closed orientation to the expanded orientation to prohibit relative rotation back to the closed orientation.

14. The expandable spinal implant of claim 10, wherein the central portions of the first and second members are generally cylindrical.

15. The expandable spinal implant of claim 10, wherein the first and second members are constructed of allograft bone.

16. An expandable spinal implant comprising:
a first member having first and second arms, the first arm of the first member being substantially parallel and transversely offset relative to the second arm of the first member; and
a second member having first and second arms, the second member being completely separate from the first member; the first arm of the second member being substantially parallel and transversely offset relative to the second arm of the second member;
the first and second members pivotally coupled to each other for relative movement between a closed position for inserting the implant into a spine and an expanded position for providing structural support to the spine, wherein the expanded position is substantially X-shaped.

17. The implant of claim 16, wherein the first arm of the first member is connected to the second arm of the first member with a first resilient element, and the first arm of the second member is connected to the second arm of the second member with a second resilient element.

18. The implant of claim 17, wherein the first and second resilient elements are aligned along an axis of rotation between the first and second positions.

19. The implant of claim 17, wherein the first and second resilient elements are leaf springs.

20. The implant of claim 16 wherein the first and second members are pivotably coupled with a leaf spring.

21. An expandable spinal implant comprising:
- a first member having a central portion and first and second arms extending from the central portion of the first member;
- a second member having a central portion and first and second arms extending from the central portion of the second member, the central portion of the second member coupled to the central portion of the first member for rotation about a rotation axis between a closed orientation for insertion into a spine and an expanded orientation for providing structural support to the spine, wherein the central portions of the first and second members form a leaf spring for arresting relative movement between the first member and the second member.

* * * * *

UNITED STATES PATENT AND TRADEMARK OFFICE
CERTIFICATE OF CORRECTION

PATENT NO. : 7,318,839 B2 Page 1 of 1
APPLICATION NO. : 10/897371
DATED : February 13, 2008
INVENTOR(S) : Marc I. Malberg et al.

It is certified that error appears in the above-identified patent and that said Letters Patent is hereby corrected as shown below:

Column 2
Line 42, insert --of-- after "view".

Column 4
Line 19, insert --in-- after "best".

Column 5
Line 43, delete "of" before "recesses".

Column 5
Line 43, insert --of-- before "cooperating".

Column 6
Line 34, "intevetrabal" should be --intervertebral--.

Column 8
Line 8, delete second occurrence of "the".

Column 8
Line 21, "1116" should be --116--.

Column 8
Line 35, "117" should be --118--.

Claim 6, column 8, line 57, change "boding" to --bonding--.

Signed and Sealed this

Thirteenth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,318,839 B2
APPLICATION NO. : 10/897371
DATED : January 15, 2008
INVENTOR(S) : Marc I. Malberg et al.

It is certified that error appears in the above-identified patent and that said Letters Patent is hereby corrected as shown below:

Column 2
Line 42, insert --of-- after "view".

Column 4
Line 19, insert --in-- after "best".

Column 5
Line 43, delete "of" before "recesses".

Column 5
Line 43, insert --of-- before "cooperating".

Column 6
Line 34, "intevetrabal" should be --intervertebral--.

Column 8
Line 8, delete second occurrence of "the".

Column 8
Line 21, "1116" should be --116--.

UNITED STATES PATENT AND TRADEMARK OFFICE
CERTIFICATE OF CORRECTION

PATENT NO. : 7,318,839 B2
APPLICATION NO. : 10/897371
DATED : January 15, 2008
INVENTOR(S) : Marc I. Malberg et al.

It is certified that error appears in the above-identified patent and that said Letters Patent is hereby corrected as shown below:

<u>Column 8</u>
Line 35, "117" should be --118--.

Claim 6, column 8, line 57, change "boding" to --bonding--.

This certificate supersedes the Certificate of Correction issued May 13, 2008.

Signed and Sealed this

Third Day of June, 2008

JON W. DUDAS
*Director of the United States Patent and Trademark Office*